(12) United States Patent  
Moehring et al.

(10) Patent No.: US 10,925,583 B1
(45) Date of Patent: Feb. 23, 2021

(54) APPARATUS AND METHOD FOR DETECTION OF COMPARTMENT SYNDROME

(71) Applicant: Jay A. Chesavage, Palo Alto, CA (US)

(72) Inventors: Mark A. Moehring, Seattle, WA (US); Jay A. Chesavage, Palo Alto, CA (US); Daniel Kreindler, Foster City, CA (US); Marc Fine, Camano Island, WA (US)

(*) Notice: Subject to any disclaimer, the term of this patent is extended or adjusted under 35 U.S.C. 154(b) by 865 days.

(21) Appl. No.: 15/619,544

(22) Filed: Jun. 12, 2017

(51) Int. Cl.
*A61B 8/08* (2006.01)
*A61B 8/00* (2006.01)

(52) U.S. Cl.
CPC .......... *A61B 8/5223* (2013.01); *A61B 8/4227* (2013.01); *A61B 8/4477* (2013.01)

(58) Field of Classification Search
CPC ........... A61B 8/00; A61B 8/12; A61B 8/4227; A61B 8/4477; A61B 8/5223
See application file for complete search history.

(56) References Cited

U.S. PATENT DOCUMENTS

| | | | |
|---|---|---|---|
| 2006/0025686 A1* | 2/2006 | Ueno | A61B 8/08 600/443 |
| 2008/0269608 A1* | 10/2008 | Anderson | A61N 7/02 600/439 |

* cited by examiner

*Primary Examiner* — Peter Luong
(74) *Attorney, Agent, or Firm* — File-EE-Patents.com; Jay A. Chesavage (57) ABSTRACT

An apparatus for the detection of compartment syndrome (CS) provides an ultrasound transducer which is operative to excite the ultrasound transducer with a transmit waveform having a center frequency. The ultrasound beam traverses through the compartments of interest, and reflections of signal through Rayleigh scattering are received, amplified, and mixed with a transmit clock to form a baseband quadrature signal, or alternatively, are sampled as RF. Reflections from the compartment volume front and rear fascia interfaces are examined for phase shift, after which an elasticity metric is generated indicating the likelihood of CS in the effected tissues.

19 Claims, 6 Drawing Sheets

*Figure 1*
Compartments of lower leg

*Figure 2*

Figure 3
Section A-A of Fig 2

Figure 4
Signal Processing

Figure 5
Example Transducer/Compartment

Figure 6

Figure 7A-1
Normal Compartment Phase Plot

Figure 7A-2
Normal Compartment Phase Plot

Figure 7B
phase difference plot (Perfusion expansion of compartment)

*Figure 8A-1*
Compartment Syndrome Phase Plot
802

*Figure 8A-2*
Compartment Syndrome Phase Plot
804

*Figure 8B*
phase difference plot (Perfusion expansion of compartment)
806

Figure 9

Delta Phase vs time through Cardiac Cycle

APPARATUS AND METHOD FOR DETECTION OF COMPARTMENT SYNDROME

FIELD OF THE INVENTION

The present invention relates to a diagnostic device for detection of Compartment Syndrome. In particular, the invention relates to the use of ultrasound combined with muscle and fascia movements in response to internal (such as cardiac cycles) and external stimulus (such as pressure forces) to determine tissue elasticity and likelihood of compartment syndrome.

BACKGROUND OF THE INVENTION

Compartment syndrome is a medical condition where the pressure inside a muscle group surrounded by fascia, known as a compartment, increases until the blood circulation inside the compartment and associated muscle groups is significantly reduced. The most common site for compartment syndrome (CS) occurrence in humans is the lower leg, and more specifically, in regions adjacent to the tibia and fibula, and the second most common site for CS occurrence is the forearm, although CS may occur in any muscle group enclosed by inelastic fascia connective tissue which forms the compartment following an injury or insult. There are four compartments in the lower human leg: the anterior (front), lateral (next to the fibula) and the deep and superficial posterior (back) compartments.

These four compartments surround the tibia and fibula. Any one of these four compartments can yield a compartment syndrome when bleeding or swelling occurs within the compartment. Compartment syndrome usually occurs after some trauma or injury to the tissues, such as muscles or bones or vessel (or all three), contained within the compartment. Bleeding or swelling within a compartment can cause an increase in pressure within that compartment. The inelastic fascia does not expand, so as pressure rises, the tissue and vessels begin to be compressed within the compartment.

This compression of enclosed muscle tissue from intra-compartmental pressure can restrict and often times stop blood flow from entering the compartment that is destined for any tissues contained within the compartment. Restriction or cessation of blood flow is termed ischemia, which can cause affected tissues to eventually die, a condition known as necrosis.

A simple working definition for a compartment syndrome is an increased pressure within a closed space which reduces the capillary blood perfusion below a level necessary for tissue viability. As noted above, this situation may be produced by two conditions. The first condition can include an increase in volume within a closed space, and the second condition is a decrease in size of the space.

An increase in enclosed compartment volume occurs in clinical settings of hemorrhage, post ischemic swelling, re-perfusion, and arterial-venous fistula. A decrease in enclosed compartment size results from a cast that is too tight, constrictive dressings, pneumatic anti-shock garments, and closure of fascial defects. As the pressure increases in the enclosed tissue, it exceeds the low intramuscular arteriolar pressure, causing decreased blood in the capillary anastomosis and subsequent shunting of blood flow from the compartment.

The clinical conditions that may be associated with compartment syndrome include the management of fractures, soft tissue injuries, arterial injuries, drug overdoses, limb compression situations, burns, post-ischemic swelling, constrictive dressings, aggressive fluid resuscitation and tight casts.

One prior art system for detection of compartment syndrome uses the insertion of a large bore needle into the compartment, the needle having a gauge size such as 16 or 14 (~2 mm, or ~0.08 inch), which is extremely painful. After insertion of the large bore needle into the compartment, a small amount of saline is injected through the needle to clear any tissue blockage of the needle which may have occurred during needle insertion, after which a pressure measurement is taken. This procedure must be repeated periodically, with the needle inserted over time to each of the several compartments for tracking of the pressures in each compartment, and the pressure trends in each (as increasing, steady, or decreasing). While compartment pressures can be measured with this conventional method, the procedure is highly invasive, and can cause tremendous pain to the patient.

In addition to causing tremendous pain, there are several other problems associated with the conventional needle pressure measurement method. First, it is very challenging for a medical practitioner to actually measure or read pressure of a compartment since the needle must be positioned at least within the interior of a particular compartment. To enter the interior of a compartment, the needle must penetrate through several layers of skin and muscle. Accordingly, it is very difficult for the medical practitioner to know if the needle has penetrated adequately through the intermediate layers to enter into the compartment. This challenge significantly increases if the diagnostic pressure measurement procedure is performed on an obese subject having significant amounts of subcutaneous fat to penetrate with the needle to reach the compartment.

Often, the medical practitioner may not have a needle accurately positioned inside a compartment which can yield a reading of the tissue adjacent to the compartment, such as muscle or skin. Such a reading of muscle or skin instead of the compartment of interest can provide the medical practitioner with elevated or depressed pressure readings that do not reflect the actual pressure contained within the compartment of interest. Moreover, the needle must be positioned separately in each compartment to be diagnostically characterized. Pressure readings inside a compartment have been shown to vary (increase) based on the depth of the reading as well as the proximity to the fracture site.

Because of the challenge medical practitioners face with precisely positioning a needle within a compartment of interest and because of the legal liability associated with mis-diagnosis of compartment syndrome, many medical schools do not provide any formal training for medical practitioners to learn how to properly place a needle within a compartment of interest for reading a compartment's pressure.

Currently, intra-compartmental pressure measurements are the only objective diagnostic tool, and a false negative (missed diagnosis of CS) results in potential limb loss, whereas a false positive results in an extremely invasive fasciotomy and large visible scarring. Conversely, for a false positive (incorrect diagnosis of CS), the treatment of CS via fasciotomy carries significant morbidity and increased risk for infection. Therefore, inaccurate and elevated pressure readings are a very difficult and potential dangerous pitfall.

Another problem associated with the training and experience required for the needle measurement method is that compartment syndrome usually occurs when tissues within the compartment are already experiencing unusual levels of swelling and pressure associated with trauma (with or without co-existent CS). With this swelling and pressure associated with trauma, the tissues do not have their normal size. Therefore, any training of a medical practitioner must be made with a patient suffering under these conditions. An asymptomatic patient without any swelling would not provide a medical practitioner with the skills to accurately assess a size of a compartment when using the needle measuring method for determining compartment pressure. Due to the trauma associated with an injury where CS may occur, normal anatomy is often not present when attempting to measure compartment pressures.

In addition to the problem of entering a compartment that may have an abnormal size or anatomy, the needle measuring method has the problem that it provides the medical practitioner with one pressure data point for a single instant of time in a single compartment. Once pressure is read by the medical practitioner, he or she usually removes the needle from the patient. The data obtained from a single measurement in time gives no information concerning the pressure trend, and the direction the intra-compartmental pressure is moving.

A further problem of the needle measurement method is that, for certain regions of the body such as the lower leg, there are four compartments to measure. This means that a patient's leg must be stuck with the large bore needle at least four times in order for a medical practitioner to rule out that a compartment syndrome exists in the lower leg. In this region, one compartment is located under a neighboring compartment such that a needle measurement may be needed in at least two locations that are very close together, but in which the medical practitioner must penetrate tissues at a shallow depth at a first location to reach the first compartment; and for reaching the second compartment that is underneath the first compartment, a large depth must be penetrated by the needle, often with the needle piercing the first compartment and then the second compartment.

Another problem, besides pain that is associated with the needle pressure measuring method, is that there is a lack of consensus among medical practitioners over the compartment pressure ranges which are believed to indicate that a compartment syndrome may exist for a particular patient. Normal compartment pressure in the human body usually approaches 4 mmHg in the recumbent position. One diagnostic metric in use indicates that a pressure measurement of 30 mmHg above diastolic blood pressure in a compartment may indicate presence of compartment syndrome. Another diagnostic metric for diagnosis of CS relies on intra-compartmental pressures of 45 mmHg or greater. However, contraindicating studies have shown patients with intra-compartmental pressures above these limits with no clinical signs of compartment syndrome. Additional studies have shown that a pressure gradient based on perfusion pressure (diastolic blood pressure minus intra-compartmental pressure) is the clinically more important indicator. Studies have shown in a laboratory setting that once the perfusion pressure drops to 10 mm Hg tissue necrosis starts to occur.

Other subjective methods for diagnosing compartment syndromes instead of the needle measuring method exist, however, they may have less accuracy than the needle measuring method because they rely on clinical symptoms of a patient. Some clinical symptoms of a patient used to help diagnose compartment syndromes include pulselessness (absence of detectable blood flow in the compartment), lack of muscle power, pain, parasthesias, and whether the surrounding flesh is cold to touch. Pain out of proportion and with passive stretch are considered the earliest and most sensitive, but both have very low specificity. One of the major drawbacks of these symptoms is that for many of them the patient must be conscious and must be able to respond to the medical practitioner. This is true for the muscle power and pain assessment. For any inebriated patients or patients who are unconscious, the pain assessment and muscle power assessment cannot be used accurately by the medical practitioner. In the setting of high energy trauma which is associated with compartment syndrome, many patients are not capable of cooperating with a good physical exam due to any number of causes including head trauma, medical treatment (including intubation), drug or alcohol ingestion, neurovascular compromise or critical and life threatening injuries to other body systems.

For the pain assessment, if a lower leg compartment syndrome exists in a patient, then the range of motion for a patient's foot or toes will be extremely limited and very painful when the patient's foot or toes are actively or passively moved. The pain from a compartment syndrome can be very immense because the muscles are deprived of oxygen from the associated loss of blood perfusion.

Another drawback of using pain to assess the likelihood of a compartment syndrome is that every human has a different threshold for pain. This means that even if someone should be experiencing a high level of pain, he or she may have a high threshold for pain and therefore, not provide the medical practitioner with a normal reaction for the current level of pain. Another problem with using pain to assess the likelihood of the existence of a compartment syndrome is that if the patient is experiencing trauma to other parts of their body, he or she may not feel the pain of a compartment syndrome as significantly, especially if the trauma to the other parts of the patient's body is more severe. This condition is termed a distracting injury. On the other hand, trauma causes the initial injury that precipitates a compartment syndrome. That initial trauma by definition will cause a baseline amount of pain that is often very difficult to separate from a potential compartment syndrome pain. These initial injuries by themselves cause significant pain, so a patient that does not tolerate pain well may present similar to a compartment syndrome without having any increased pressures simply because they react vehemently to painful conditions.

The preferred standard of treatment for Compartment Syndrome is a fasciotomy, which is performed in order to release the pressures in one or more compartments surrounding the bones of the leg according to a technique known in the art in order to alleviate a compartment syndrome that was diagnosed. For the lower leg, this surgical procedure includes an incision that is made along the length of the leg and is generally as long as the compartments contained within the leg. Typically the incision is made on either side of the tibia which extends deep into the fascia, which extend from near the knee to near the ankle on each side of the leg.

This procedure is very invasive and it often leaves the patient with severe scars and venous congestion once healed. Also, the procedure increases a patient's chances of receiving an airborne infection because the incisions made on either side of the leg are usually left open for several days in order to allow for the swelling and excess bleeding to subside. Fasciotomies transform a closed fracture (one in which the skin is intact and minimal risk of infection) to an open fracture. Open fractures have a much higher risk of bone infections which requires multiple surgical debridements and ultimately amputation in some cases in order to appropriately treat. Additionally, some wounds cannot be closed and require skin transfers, or skin grafts, from other parts of the body, usually from the anterior thigh.

Therefore, it is quite apparent that accurately diagnosing compartment syndrome is critical because any misdiagnosis can lead to significant morbidity. A missed compartment syndrome can result in an insensate and contracted leg and foot. Accordingly, fasciotomy is considered a highly invasive procedure which exposes the patient to many additional health risks, and should not be performed in the absence of a definitive diagnosis of compartment syndrome.

Additionally, time is an important factor in the evaluation of these patients. Ischemic muscle begins to undergo irreversible changes after about six hours of decreased perfusion. Once irreversible changes or necrosis occur, a fasciotomy should not be performed. Fasciotomies in the setting of dead muscle only increase the risk for severe infections and other complications. Late fasciotomies have been shown to have approximately a 50-75% risk of complication. Therefore, fasciotomies need to be performed early but judiciously in patients that are often unresponsive or uncooperative in order to prevent severe morbidity.

In light of the state of the art for the diagnosis of CS, there is a need for a non-invasive, real time method and system that monitors the onset, extent, and progression of compartment syndrome.

OBJECTS OF THE INVENTION

A first object of the invention is a system for the detection of compartment syndrome, the system having one or more ultrasound transducers positioned on a human limb, the system selecting, in sequence, one or more ultrasound sensors, and for a selected sensor, generating a transmit pulse burst with a center frequency, optionally converting the received signal to a baseband frequency by mixing with the transmit frequency, detecting a front surface and a rear surface of one or more compartments, or alternatively taking phase measurements throughout the compartment or acquisition interval, comparing the phase of the reflected signals over time and depth over the one or more compartments being characterized, thereby measuring positional displacements of the enclosed compartment or the boundaries of the compartment, thereafter forming a difference in displacement of the compartment sampled positions over time, and estimating an elasticity from the displacement measurements over time, using either cardiac rhythm and perfusion cycles or externally applied pressure as the underlying generator of positional displacements being measured.

A second object of the invention is a system for the detection of compartment syndrome, the system ultrasonically measuring the phase of reflected ultrasound over a measurement volume, using the phase measurements over the measurement volume to estimate the contraction and expansion of individual compartments with respect to cardiac pumping cycles, thereafter forming an estimate of elasticity for each compartment from the positional displacements associated with expansion or contraction of the measurement volume which includes the compartments being characterized.

A third object of the invention is a method for detection of compartment syndrome, the method having the steps:

providing ultrasonic pulses into a region of interest, the ultrasonic pulses transmitted with a center frequency;

receiving ultrasonic reflections from the region of interest, establishing a phase difference between the reflected signal and the transmitted ultrasonic pulse at one or more temporal measurement locations, each transmit and receive cycle forming a data acquisition cycle comprising a plurality of sampled phase values;

establishing boundaries of structures being imaged by comparison of the data acquisition cycles;

for each structure, using the phase differences over several data acquisition cycles to establish a contraction and expansion distance of the structure, the expansion and contraction caused by an external force such as external palpation or a cardiac perfusion cycle from a subject cardiac pumping cycle;

for each region, establishing an elasticity metric, the elasticity metric providing an indication of likelihood of extent of compartment syndrome.

SUMMARY OF THE INVENTION

An ultrasound system provides one or more pulses of ultrasonic energy into an enclosed limb having compartments. The ultrasonic pulses are transmitted using a burst of acoustic energy having a center frequency. During a receive acquisition window following the transmit burst, a series of samples of phase estimates are taken indicating the phase change from the transmit clock, and by comparison of acquisition events over time, phase offsets between the transmitted and received ultrasound pulses are formed, which are collectively used to estimate the displacement of each identified compartment. The acquisition cycle sequence of phase measurements are synchronized to an external pressure event, or to a cardiac cycle to estimate perfusion and/or elasticity of each compartment being examined. A determination of compartment syndrome may be made through the use of a CS metric such as a comparison of displacement expansion or contraction per unit length, comparing this CS metric from one compartment to another, or alternatively, comparing the CS metric from a compartment of one limb to an associated compartment of another limb.

BRIEF DESCRIPTION OF THE DRAWINGS

FIGS. 7A-1 and 7A-2 show phase plots for a particular depth collected over many transmit events and two cardiac cycles for a normal compartment.

FIGS. 8A-1 and 8A-2 show a plot for a particular depth collected over many transmit events and two cardiac cycles for a compartment having compartment syndrome.

DETAILED DESCRIPTION OF THE INVENTION

Figure 1:
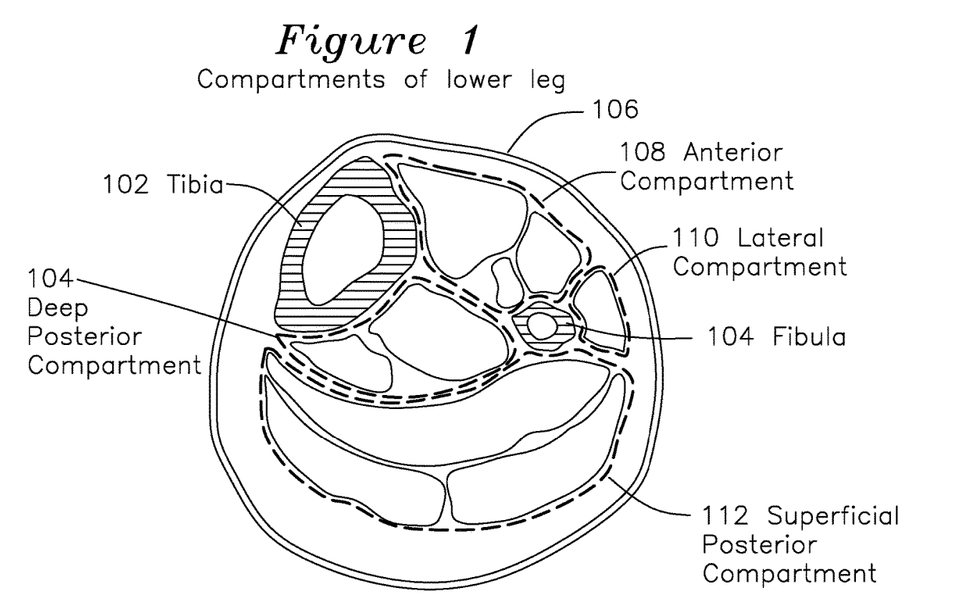
FIG. 1 shows a cross section view of compartments of the lower leg.

FIG. 1 shows a cross section view showing the compartments of the lower leg. Tibia 102 and fibula 104 are bones surrounded by anterior compartment 108 enclosing three muscle groups, lateral compartment 110 contains a single muscle, superficial posterior compartment 112 contains three muscle groups, and deep interior compartment 104 contains two muscle groups. Each compartment is defined by fascia, connective tissue which surrounds and encloses the muscle groups. Arteries and veins (not shown) pass into the compartments to oxygenate the muscle tissue via blood perfusion through the capillary beds in the muscle groups.

Figure 2:
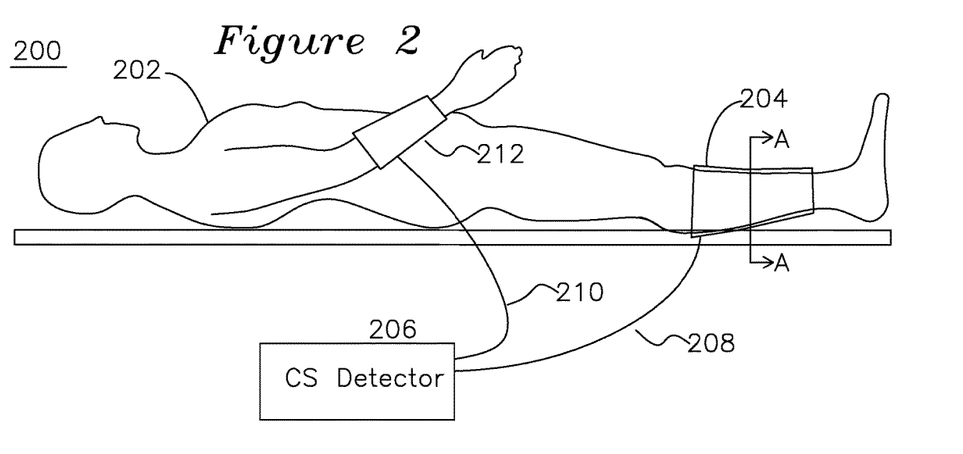
FIG. 2 shows a subject wearing an ultrasonic sensor on the lower leg and on the forearm for the detection of compartment syndrome.
Figure 3:
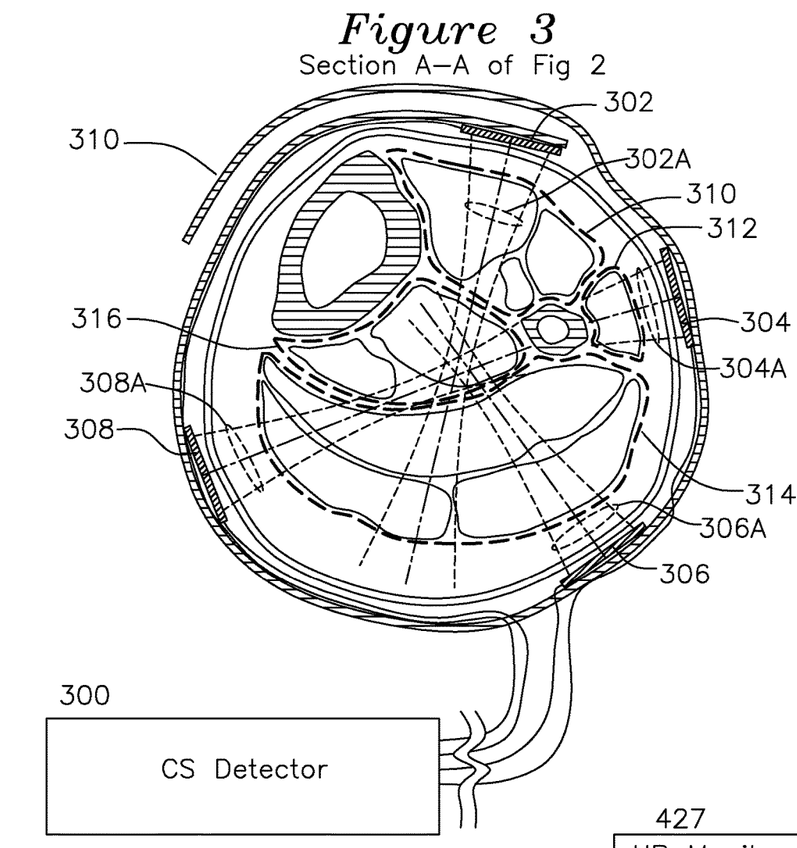
FIG. 3 shows a cross section view of compartments of the legs being characterized by ultrasound sensors.

FIG. 2 shows a subject 202 wearing a first sensor array 204 on a lower leg, and sensor array 212 on a forearm, each sensor array 202 and 212 coupled to a CS detector 206 either wirelessly (not shown) or with cables 208 and 210, respectively. FIG. 3 shows an example lower leg sensor array 204, which may be viewed as cross section A-A of FIG. 2 with lower leg anatomy shown for reference. One or more ultrasound transducers, such as 302, 304, 306, and 308 are positioned radially, each coupling ultrasound acoustic waves through the skin and forming acoustic beams 302A, 304A, 306A, and 308A, with the individual ultrasound beams coupled through one or more compartments 310, 312, and 314 to be characterized in the present example. A normal compartment has associated baseline elasticity and expansion/contraction cycles in response to each cardiac cycle. Accordingly, each compartment will detectably expand and contract in response to cardiac cycles of increasing and decreasing blood pressure, and the extent of such contraction and expansion will be related to the basal internal pressure which is present inside the compartment. A compartment with compartment syndrome will have elevated interior pressure, and be subject to significantly less expansion and contraction than a compartment without CS. In one example of the invention, each ultrasound beam is used to separately interrogate each compartment with the transmit and receive signal processing performed by CS detector 300. In another example of the invention, the boundaries of the compartments are identified and the displacement of the boundaries are characterized. In another example of the invention, the volume of each compartment is identified by its time progression of expansion and contraction over a number of cardiac perfusion cycles and in comparison to adjacent compartments which are also expanding and contracting in response to cardiac perfusion cycles. In another example of the invention, an external pressure impulse is applied and the response to the external pressure is observed using phase changes of the compartment volume over time, as evidenced by phase changes in the reflected signal over several transmit receive cycles.

Figure 4:
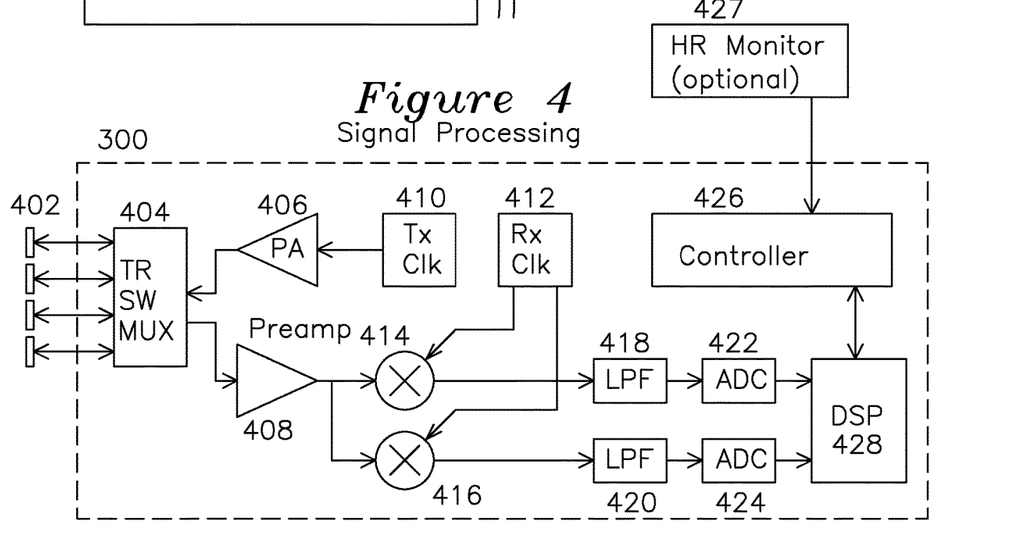
FIG. 4 shows a block diagram for signal processing of detection of compartment syndrome.

FIG. 4 shows a block diagram for example signal processing. A plurality of transducers 402 are available, at least one of which is individually selected by a transmit/receive switch multiplexer 404, with transmit signals derived from a transmit clock generator 410 and having one or more cycles at a center frequency coupled from a power amplifier 406, and with signals received from the transducers directed to a preamplifier 408, thereafter to quadrature mixers 414 and 416, which mix the received transducer signals with a receive clock 412 which is the same frequency as the burst from the TX clock generator 410, thereby providing baseband quadrature signals. These signals are low pass filtered 418 and 420, and digitized 422 and 424, and delivered to a digital signal processor 428 which generates a sequence of samples over each acquisition cycle preferably equal to the temporal extent of the compartments. The DSP 428 extracts the phase offsets of the received signals at various depths and saves the phase offset measurements of each transmit event into an array of phase measurements for comparison over time, or alternatively over one or more cardiac perfusion cycles. The variation in received signal phase over regions of the imaged area over cycles of cardiac output represent the expansion and contraction of the compartment, which may be further processed to extract an elasticity metric, which would typically be scaled by the extent over which the range gate measurement was made, such as $$\frac{\Delta\varphi 1(t1) - \Delta\varphi 2(t2)}{d}$$

where d is the separation distance between regions of phase measurement, and φ1(t) and φ2(t) are the phase measurements for particular depths associated with times t1 and t2. In one example of the invention, t1 and t2 correspond to a distal and proximal compartment fascia boundary with respect to an associated transducer. In another example of the invention, the phase of the samples over time are characterized to identify each compartment and associated elasticity and/or perfusion. In another example of the invention, tissue phase measurements over the depth of an ultrasound beam are taken over several cardiac perfusion cycles of a limb suspected of having compartment syndrome to form the compartment syndrome metric for the first limb, and subsequent tissue phase measurements over the depth of an ultrasound beam are taken over several cardiac perfusion cycles of a different limb of the same subject where compartment syndrome is not suspected, thereby establishing a reference baseline for the compartment syndrome metric. In another embodiment of the invention, a heart rate monitor 427, such as an EKG or blood plethysmograph, is coupled to the subject, and the blood perfusion cycles are synchronized by the controller 426 to the heart rate with a delay to improve the identification of perfusion cycles with cardiac cycles. Such synchronization may be performed by first determining the delay between a cardiac peak and a perfusion expansion peak (maximum expansion of the compartment), and subsequently applying a weighting factor which is greater during an expected perfusion expansion cycle than during other times.

Figure 5:
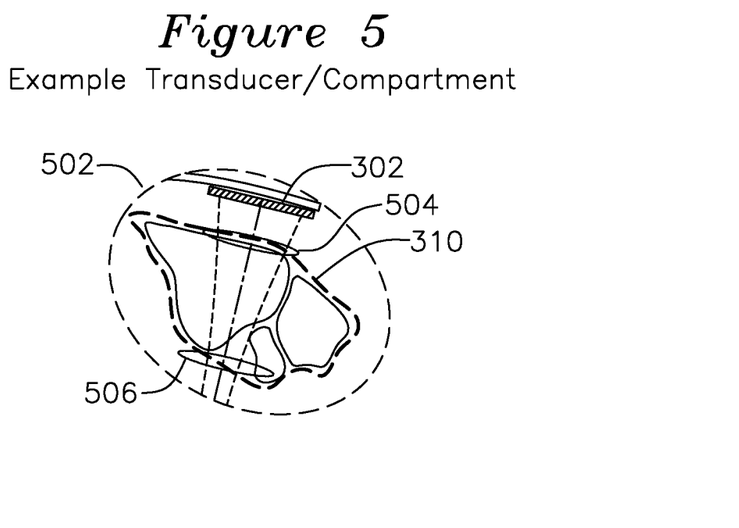
FIG. 5 shows a single transducer making a single compartment measurement from FIG. 3.
Figure 6:
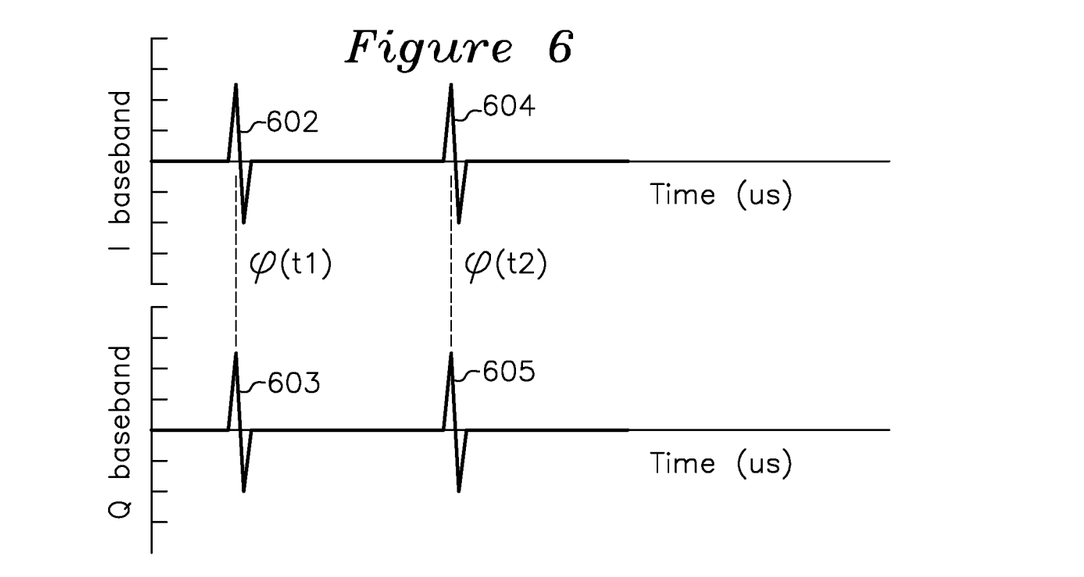
FIG. 6 shows plots of I (inphase) and Q (quadrature) signals from the ultrasonic transducer of FIG. 5 from a single transmit event.

FIG. 5 shows an example of the invention where transducer 304 is directing ultrasound energy to compartment 310 which has a proximal fascia interface 504 and a distal fascia interface 506. When the transducer 302 is provided with a single cycle transmit excitation pulse from 410 of FIG. 4, the acoustic wave which is emitted by transducer 302 returns a first reflection 602,603 and second reflection 604, 605 at different times associated with the reflections from front interface 504 and rear interface 506, which are distinguishable as having occurred at times t1 and t2, respectively.

Figure 7A:
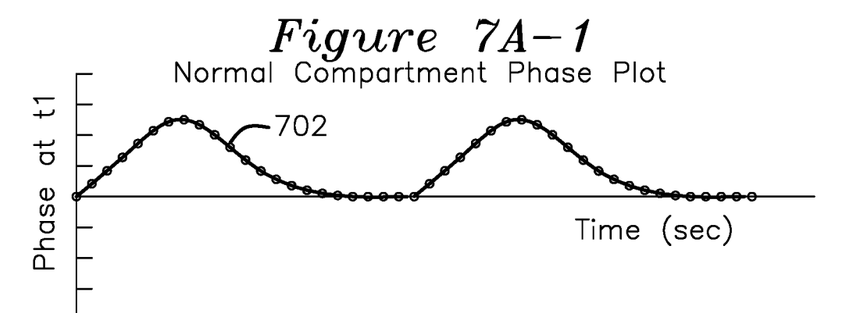
Figure 7A:
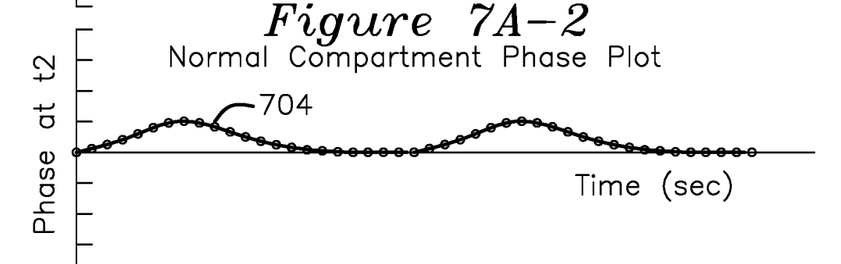
Figure 7B:
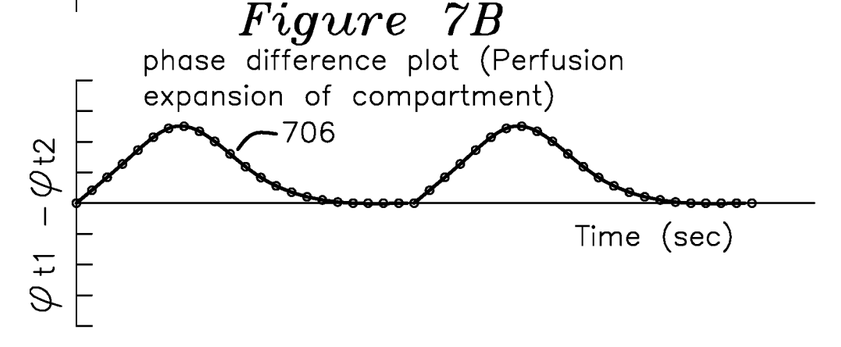
FIG. 7B shows a plot of the phase difference from the two waveforms of FIGS. 7A-1 and 7A-2 for a normal compartment.

FIGS. 7A-1 and 7A-2 shows the progression of phase at time t1 waveform 702 corresponding to a compartment fascia (ultrasound entering) interface near the transducer, and waveform 704 is the same compartment but opposite (ultrasound existing) interface of fascia at time t2 for the same compartment. The respective phase at t1 and t2, over many samples, shown as 17 samples for each cardiac cycle of FIGS. 7A-1, 7A-2, and 7B, will reflect the inflation and deflation of the compartment, as evidenced by the front compartment interface and rear compartment interface moving over different respective displacement extents over each cardiac cycle. The same-direction movement as evidenced by the respective phases 702 and 704 may indicate that the associated compartment is being displaced by a subsequent compartment, which displacement effect is removed by subtracting the waveform 702 from 704. With respect to FIG. 3, such a result may be observed when transducer 302 is used after a transmit event to receive reflections from the interface near compartment 310 at t1, and reflections from the interface far compartment 310 at t2, where compartment 316 is expanding and contracting, thereby displacing compartment 310 and causing the observed movement of the entire compartment 310. Subtracting these two displacement profiles results in the phase plot of FIG. 7B, which shows a phase plot for a normal compartment, where, for an example 2 Mhz transducer and an acoustic propagation velocity of 1550 mt/second in muscle, or 1.2 cycles per mm of tissue, the resolution for a detected phase change of one degree of phase is 2.3 um of fascia displacement. Transmit cycles are typically at a fixed period, and may have 1 to 100 cycles, the number of cycles typically corresponding to an extent of the compartment being interrogated ultrasonically, where the transmit burst may be less than 10% the extent of the compartment. For example, for a compartment having an entry fascia boundary to exit fascia boundary of 50 mm, and a 2 Mhz transmit frequency, the transmit pulse extent should be less than 5 mm, or 4 cycles at 2 Mhz. These are approximate guidelines, and are dependent on the particular transducer frequency.

Figure 8A:
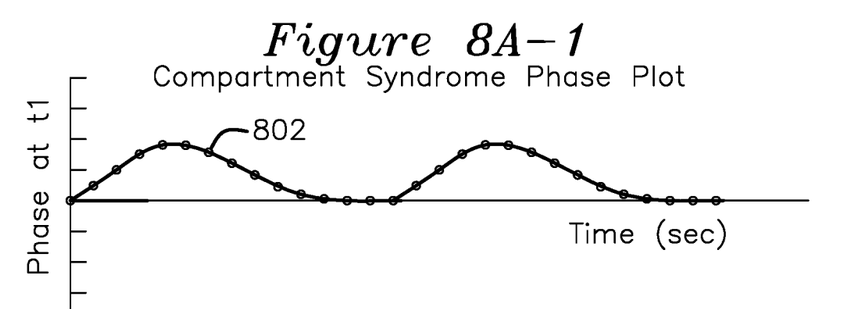
Figure 8A:
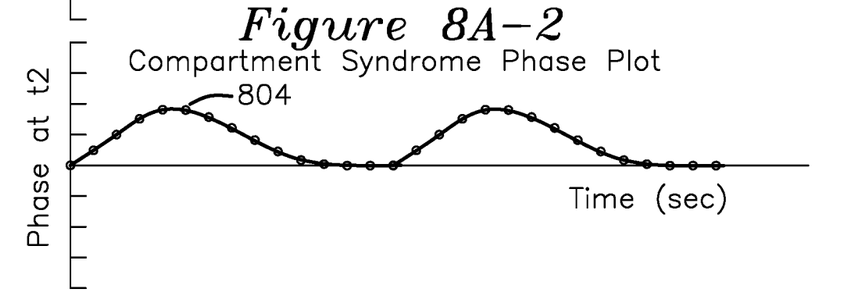
Figure 8B:
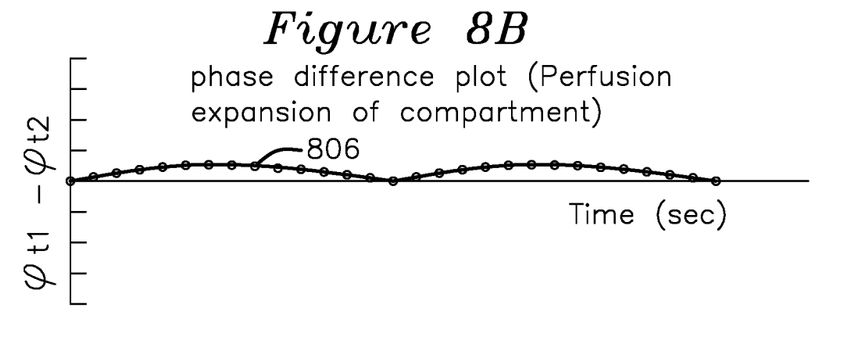
FIG. 8B shows a phase different plot derived from the plots of FIGS. 8A-1 and 8A-2.

FIGS. 8A-1 and 8A-2 show the progression of phase at t1 waveform 802, and t2 waveform 804, respectively over 14 samples of a cardiac cycle, for which the phase difference 806 of FIG. 8B shows greatly reduced displacement of the compartments, indicating a likely compartment syndrome for the compartment which the transducer was measuring.

Figure 9:
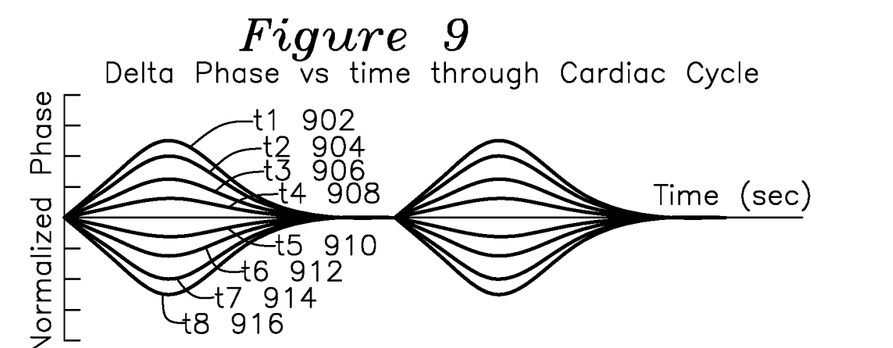
FIG. 9 shows phase sample points over data acquisition samples which span two cardiac cycles.

FIG. 9 shows plots for phase measurements through two cardiac cycles for an example measurement of a central compartment which has a phase repetitively sampled at various times t1 through t8, t1 corresponding to the surface of the compartment closest to the transducer and in its beam path, and t8 corresponding to the opposite surface of the compartment along the same ultrasound beam path. The times t1 through t8 relate to the time of flight for ultrasound propagation velocity, which is approximately 1.5 mm/us). The present example shown in FIG. 9 may correspond to the phase displacements associated with the ultrasound beam 302A interacting with the near (corresponding to t1) and far (corresponding to t8) interfaces of compartment 316 of FIG. 3, when the acoustic wave formed by transducer 302 is partially reflected by Rayleigh scattering through the compartment 316. For this example, the tissue region between sample times t4 and t5 is neutral in displacement (and phase change), whereas the near fascia interface at time t1 and far fascia interface at time t8 experience the greatest shifts movements, and hence, phase (based on the earlier computation of $$360 \text{ degrees of phase} = \frac{1500 \text{ mt/s}}{f}.$$

For f=1 Mhz, 360 degrees of phase is 1.5 mm of displacement, so a resolution of 3.6 degrees corresponds to 15$u$ displacement in the sampled region of the compartment. By taking a series of RF or baseband signal acquisition events over a time duration which covers multiple compartments in each acquisition event, finding the several changes in displacement direction over a few cardiac cycles (indicating center of each compartment), it is possible to use the algorithms described to determine the elasticity and compartment syndrome metric for each compartment non-invasively.

In another variation of the invention, the apparatus and method for estimation of compartment syndrome metric may be combined with pressure the subject develops by "bearing down" to increase abdominal pressure, such as that generated by the well-known valsalva maneuver. Such increased abdominal pressure may cause a momentary decrease in systolic and diastoic pressure, followed by a hypertensive overshoot after release of the strain, which modulation in blood pressure may be also used in combination with the previously described measurement techniques to observe the elasticity of the compartments being characterized, where reduced elasticity (increased internal strain) is associated with compartment syndrome, and increased elasticity (reduced internal strain) is associated with a normal compartment physiology.

Figures 10, 10A:
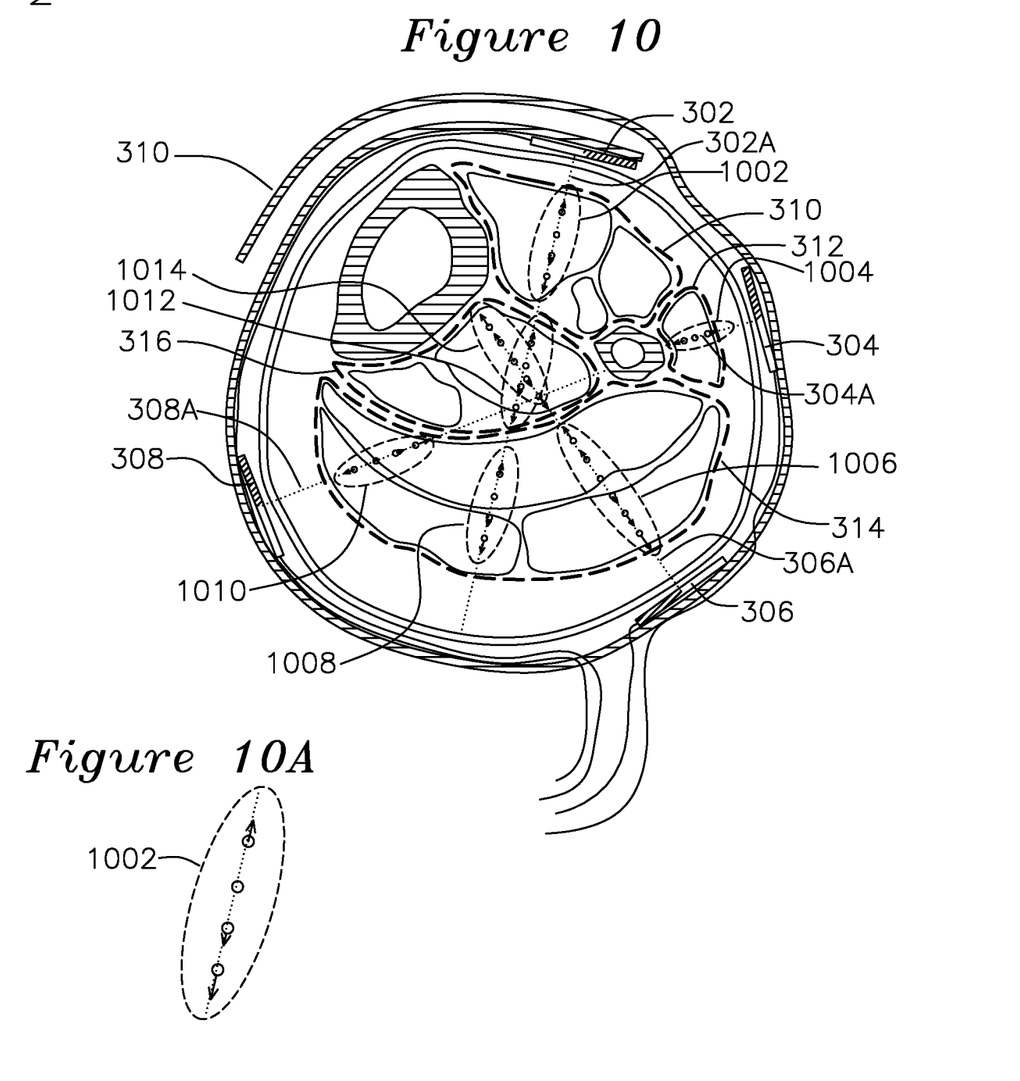
FIG. 10 shows a cross section view as in FIG. 3 with perfusion vector derived from transducer phase measurements showing magnitude of tissue displacement from cardiac perfusion cycle.
FIG. 10A is a detail view of FIG. 10 showing tissue displacement.

FIG. 10 shows a related example for FIG. 9 showing the corresponding anatomical section view of FIG. 3 for individual acoustic beam axes 302A, 304A, 306A, 308A from respective transducers 302, 304, 306, and 308. On each beam is superimposed a series of vectors shown as a tail circle (sample tissue position at ebb of cardiac perfusion cycle), and an arrow indicating magnitude and direction of maximum cardiac perfusion displacement of the particular sampled point throughout the cardiac perfusion cycle. In a normal compartment without a compartment pressure present, the compartment tissues will migrate generally radially outward from the center of a respective compartment in response to each cardiac perfusion cycle, with the transducer and controller computing tissue phase shifts along the respective transducer beam axis of acoustic propagation in response to cardiac perfusion cycles. Examination of reflected acoustic energy from transducer 302 provides phase responses along axis 302A which include the phase shift responses of 1002 for compartment 310, phase shift responses 2012 for compartment 316, and phase shift responses 1008 for compartment 314. Similarly, transducer 304 with beam axis 304A provides phase shifts 1004 of compartment 312, and transducer 306 provides phase shift responses 1006 of compartment 314 and 1014 of compartment 316, with transducer 308 providing phase shift responses 1010 of compartment 314. FIG. 10A shows an expanded view of a single region 1002 of beam 302A. For a normal compartment, each phase shift response may include a generally radial expansion from the center of the compartment, as well as a uniform compartment-wide offset (for example, as the result of an adjacent normal compartment pushing on the edge of a subject compartment having compartment syndrome) which may be subtracted to estimate the growth and shrinkage of the subject compartment. A compartment syndrome metric may include the amount of radial expansion per unit length within the compartment or near its center. In one example, a compartment syndrome metric is formed by identifying the center of the compartment by finding a null (not displaced) region at the center region of the compartment surrounded by increasing radial expansion over several cardiac cycles, and examining the radial expansion of surrounding tissue, optionally to the outer extents of a particular compartment. Alternatively, the process may examine the displacement in each compartment and determine a threshold value for expansion/distance, or alternatively examine the displacement and measure linearity of expansion over the extent of expansion to form a compartment syndrome metric. In another embodiment of the invention, one or more of the previously described compartment syndrome metrics may be estimated from the phase measurement on one limb and compared to the same compartment syndrome metric from a healthy limb of the same individual. A compartment which is afflicted with compartment syndrome may exhibit reduced or minimal radial expansion compared to another compartment which has not developed sufficient fluctuations in internal cardiac perfusion pressure to have the same extent of tissue expansion, as measured using ultrasound phase through the volume of the compartment.

The scope of the invention is not limited to the particular embodiments and examples shown, but is defined by the claims which follow.

We claim:

1. An apparatus for generation of a compartment syndrome metric, the apparatus comprising:
    an adjustable cuff for encircling a limb having compartments, the adjustable cuff having one or more transducers positioned along an inner surface of the cuff and configured to direct acoustic energy to limb compartments;
    a pulse transmitter generating a burst of a periodic signal at a center frequency, the periodic burst coupled to the one or more transducers, the pulse transmitter forming an excitation to the one or more transducers sufficient to generate a traveling acoustic wave into limb compartments to be characterized;
    the ultrasound transducer receiving reflected acoustic energy from compartments to be characterized and mixing reflected acoustic energy with the transmit center frequency during a receive acquisition duration to form a series of phase measurements;
    a signal processor comparing the series of phase measurements of the receive acquisition to a predecessor series of phase measurements or a subsequent series of phase measurements to form a phase estimate for at least two time intervals in the receive acquisition duration corresponding to two or more regions of a compartment;
    the signal processor identifying at least one compartment center, compartment extent, and variation in compartment extent based on the phase estimate;
    the signal processor computing a compartment syndrome metric from the variation in compartment extent over at least one cardiac cycle.

2. The apparatus of claim 1 where the center frequency is in the range of 500 Khz to 10 Mhz.

3. The apparatus of claim 1 where the receive acquisition duration over the at least two time intervals includes a physical extent of at least one compartment of a limb.

4. The apparatus of claim 1 where a particular one of the one or more transducers is active for a particular receive acquisition duration.

5. The apparatus of claim 1 comprising one or two transducers.

6. The apparatus of claim 1 where the receive acquisition duration corresponds to a spatial extent of more than one compartment.

7. The apparatus of claim 6 where in the series of phase measurements, each phase measurement corresponds to a phase for a particular depth, and each phase measurement compared to a corresponding phase measurement preceding and succeeding the particular phase measurement for the particular depth, and where a compartment center of each individual compartment is identified by a reversal of phase direction, the signal processor thereafter identifying each compartment by expansion and contraction of a compartment extent in response to a cardiac cycle, and forming the compartment syndrome metric based on comparing the associated expansion and contraction of the phase estimates divided by the spatial separation distance between the phase estimates.

8. The apparatus of claim 1 where the pulse transmitter and the signal processor are coupled to a single transducer of the one or more transducers during the at least one cardiac cycle.

9. The apparatus of claim 1 where the pulse transmitter is coupled to one of the one or more transducers during a transmit duration and the signal processor is coupled to a different one of the one or more transducers during a receive acquisition duration.

10. The apparatus of claim 1 where the signal processor is operative on digitized samples of the receive acquisition duration.

11. The apparatus of claim 1 where the signal processor is operative on a baseband signal formed by quadrature mixing a signal received from the one or more transducers with an inphase and quadrature signal at the transmit center frequency.

12. The apparatus of claim 11 where a displacement direction is derived from a respective phase relationship between inphase and quadrature mixer output, the displacement direction used to determine the variation in compartment extent.

13. The apparatus of claim 1 where the compartment syndrome metric computed by the signal processor is estimated from a displacement distance and direction over a cardiac cycle using a plurality of samples from the one or more transducers during the receive acquisition duration, the displacement derived from the series of phase measurements.

14. The apparatus of claim 1 where the compartment center and compartment extent are identified by the magnitude and direction of displacement distance derived from a received signal phase variance with respect to the transmitted signal.

15. A method for detection of compartment syndrome (CS), the method comprising:
    transmitting bursts of ultrasound energy at a center frequency into a subject to be characterized;
    receiving reflected ultrasound energy and comparing the received ultrasound energy to the center frequency to determine phase shifts at a plurality of sample points in an acquisition cycle;
    converting the phase shifts to a displacement distance and direction for each of the sample points of an acquisition cycle;
    accumulating acquisition cycles through at least one cardiac cycle;
    comparing the displacement distance for each sample point corresponding to a particular depth for the sample points corresponding to other particular depths;
    identifying compartment centers and extents from the displacement distance comparison;

forming a compartment syndrome metric for each compartment based on the displacement distance and extent for each identified compartment.

16. The method of claim 15 where the transmitted burst has a fixed period, and a duration of the transmitted burst corresponds to less than 10% of a spatial extent of a compartment being examined.

17. The method of claim 15 where conversion of phase shifts to distance and direction is done using baseband quadrature mixing of a transmit frequency with the received signal from the transducer.

18. The method of claim 15 where forming a compartment syndrome metric further comprises examining a sequence of phase measurements to identify relative movement vectors corresponding to spatial displacement over a cardiac cycle of an imaged extent, the compartments identified by a displacement of the relative movement vectors, the relative movement vectors being resolved to a compartment center and compartment displacement extent over the at least one cardiac cycle;

the compartment syndrome metric selected to be at least one of:

a magnitude of the movement vectors at the compartment displacement extent;

comparison of a difference in movement vectors from an imaged limb compared to a reference limb of an imaged subject;

determining an average displacement distance over the compartment and subtracting the average displacement distance from all movement vectors in a region.

19. The method of claim 15 where the transmitting bursts of ultrasound energy and the receiving reflected ultrasound energy is operative on one or more transducers.

* * * * *